US006175001B1

(12) United States Patent
Barbas et al.

(10) Patent No.: US 6,175,001 B1
(45) Date of Patent: *Jan. 16, 2001

(54) FUNCTIONALIZED PYRIMIDINE NUCLEOSIDES AND NUCLEOTIDES AND DNA'S INCORPORATING SAME

(75) Inventors: Carlos F. Barbas, Del Mar; Sakthiel Kandasamy, San Diego, both of CA (US)

(73) Assignee: The Scripps Research Institute, La Jolla, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/173,672

(22) Filed: Oct. 16, 1998

(51) Int. Cl.$^7$ .................... C07H 21/04; C07H 19/073; C07H 19/10

(52) U.S. Cl. .................. 536/23.1; 536/26.23; 536/26.26; 536/26.8; 536/28.52; 536/28.55

(58) Field of Search .................... 536/23.1, 26.8, 536/28.52, 28.55, 26.23, 26.26

(56) References Cited

U.S. PATENT DOCUMENTS

| | | | |
|---|---|---|---|
| 4,711,955 | * 12/1987 | Ward et al. | 536/24.3 |
| 4,948,882 | * 8/1990 | Ruth | 536/26.6 |
| 5,013,831 | * 5/1991 | Stravrianopoulos | 536/23.1 |
| 5,241,060 | * 8/1993 | Engelhardt et al. | 536/23.1 |
| 5,684,142 | * 11/1997 | Mishra et al. | 536/22.1 |

FOREIGN PATENT DOCUMENTS

| | | |
|---|---|---|
| 2210031 | * 1/1998 | (CA) . |
| 0818460 | * 7/1997 | (EP) . |

OTHER PUBLICATIONS

Pomerantz et al., "Deconvolution of Combinatorial Oligonucleotide Libraries by Electrospray Ionizaation Tandem Mass Spectrometry," *Journal American Chemical Society*, 119(17), 3861–3867 (Apr. 30, 1997).*

Yu, et al., "Cyanine dye dUTP analogs for enzymatic labeling of DNA probes", *Nucleic Acids Research* 22 (15):3226–3232 (1994).

Kovács, et al., "Simple Synthesis of 5–Vinyl–and 5–Ethynyl–2'–Deoxyuridine–5'–Triphosphates", *Tetrahedron Letters* 29 (36): 4525–4528 (1998).

Langer, et al., "Enzymatic synthesis of biotin–labeled polynucleotides: Novel nucleic acid affinity probes", *Proc. Natl. Acad. Sci. USA* 78:6633–6637 (1981).

Cook, et al., "Synthesis and hybridization of a series of biotinylated oligonucleotides", *Nucleic Acids Research* 16 (9):4077–4095 (1988).

Aurup, et al., 2'–Fluoro–and 2'–deoxynucleoside 5'–Triphosphates as Substrates for T7 RNA Polymerase, *Biochemistry* 31(40):9636–9641 (1992).

Limbach, et al., "Summary: the modified nucleosides of RNA", *Nucleic Acids Research* 22 (12):2183–2196 (1994).

Dewey, et al., "The RNA World: Functional Diversity in a Nucleoside by Carboxyamidation of Uridine", *Nucleosides & Nucleotides* 15 (10): 1611–1617 (1996).

Dewey, et al., "New Uridine Derivatives for Systematic Evolution of RNA Ligands by Exponential Enrichment", *J. Am. Chem. Soc.* 117:8474–8475 (1995) (Issue No. 32).

Crouch, et al., "Synthesis of 2'–Deoxyuridine Nucleosides with Appended 5–Position Carbonyl Cross–Linking Groups", *Nucleosides & Nucleotides* 13 (4): 939–944 (1994).

Eaton, et al., "Ribonucleosides and RNA", *Annu. Rev. Biochem.* 64:837–863 (1995).

Lorsch, et al., "Chance and Necessity in the Selection of Nucleic Acid Catalysts", *Acc. Chem. Res.* 29:103–110 (1996) (Issue No. 2).

Breaker, "In Vitro Selection of Catalytic Polynucleotides", *Chem. Rev.* 97:371–390 (1997) (Issue No. 2).

Jäschke, et al., "In Vitro Selected Oligonucleotides as Tools in Organic Chemistry", *Synlett* 6:825–833 (1999).

Tarasow, et al., "Characteristics of an RNA Diels –Alderase Active Site", *J. Am. Chem. Soc.* 121: 3614–3617 (1999) (issue No. 15).

Rawls, "Catalytic DNAs", *C&EN* (Feb. 3, 1997), pp. 33–35.

Eaton, et al., "Let's get specific: the relationship between specificity and affinity", *Chemistry & Biology* 2 (10):633–638 (1995).

Williams, et al., "Function of specific 2'–hydroxyl groups of guanosines in a hammerhead ribozyme probed by 2' modifications", *Proc. Natl. Acad. Sci. USA* 89:918–921 (Feb., 1992).

Santoro, et al., "Mechanism and Utility of an RNA–Cleaving DNA Enzyme", *Biochemistry* 37:13330–13342 (Aug. 29, 1998).

Sakthivel, et al., "Expanding the Potential of DNA for Binding and Catalysis: Highly Functionalized dUTP Derivatives That Are Substrates for Thermostable DNA Polymerases", *Angew. Chem. Int. Ed.* 37 (20):2872–2875 (1998).

Santoro, et al., "A general purpose RNA–cleaving DNA enzyme", *Proc. Natl. Acad. Sci. USA* 94:4262–4266 (Apr., 1997).

Breaker, et al., "A DNA enzyme that cleaves RNA", *Chemistry & Biology* 1: 223–229 (Dec., 1994).

Joyce, "Nucleic acid enzymes: Playing with a fuller deck", *Proc. Natl. Acad. Sci. USA* 95: 5845–5847 (May, 1998).

(List continued on next page.)

Primary Examiner—Gary Geist
Assistant Examiner—L. Eric Crane
(74) Attorney, Agent, or Firm—Thomas E. Northrup (57) ABSTRACT

Modified pyrimidine nucleotides derivatized at C5 to contain a functional group that mimics the property of a naturally occurring amino acid residues are provided. DNA molecules containing the modified nucleotides are also provided.

12 Claims, 4 Drawing Sheets

OTHER PUBLICATIONS delCardayrè, et al., "Structural Determinants of Enzymatic Processivity", *Biochemistry* 33 (20): 6031–6037 (May 24, 1994).

Pyle, "Ribozymes: A Distinct Class of Metalloenzymes", *Science* 261: 709–714 (Aug. 6, 1993).

Symons, "Ribozymes", *Current Opinion in Structural Biology* 4: 331–336 (1994).

Breaker, et al., "Inventing and improving ribozyme function: rational design versus iterative selection methods", *Tibtech* 12: 268–275 (Jul., 1994).

Joyce, "Amplification, mutation and selection of catalytic RNA", *Gene* 82: 83–87 (1989).

Chapman et al., "*In vitro* Selection of Catalytic RNAs," *Current Opinion in Structural Biology,* 4, 618–622 (1994).*

* cited by examiner

FUNCTIONALIZED PYRIMIDINE NUCLEOSIDES AND NUCLEOTIDES AND DNA'S INCORPORATING SAME

TECHNICAL FIELD OF THE INVENTION

The field of this invention is nucleotide chemistry. More particularly, the present invention pertains to modified and functionalized pyrimidines and DNA molecules incorporating such nucleotides.

BACKGROUND OF THE INVENTION

Nucleic acid libraries provide tremendous opportunities for the selection of novel ligands and catalysts since the polymerase chain reaction, PCR, allows for the synthesis and selection of libraries containing more than $10^{14}$ different molecules. There are now many examples of nucleic acids that have been selected to bind proteins and small molecules and to catalyze a limited set of reactions (S. E. Osborne, A. D. Ellington, Chem. Rev. (Washington, D.C.) 1997, 97, 349–370; M. Famulok, J. W. Szostak, Angew. Chem. 1992, 104, 1001–11; Angew. Chem.Int. Ed. Engl. 1992, 31, 979–88; L. Gold, B. Polisky, O. Uhlenbeck, M. Yarus, Annu. Rev. Biochem. 1995, 64, 763–97; R. R. Breaker, Chem. Rev. (Washington, D.C.) 1997, 97, 371–390; R. R. Breaker, Curr. Opin. Chem. Biol. 1997, 1, 26–31; J. R. Lorsch, J. W. Szostak, Acc. Chem. Res. 1996, 29, 103–10; R. R. Breaker, G. F. Joyce, Chem. Biol. 1994, 1, 223–9; B. Cuenoud, J. W. Szostak, Nature (London) 1995, 375, 611–14; R. R. Breaker, G. F. Joyce, Chem. Biol. 1995, 2, 655–60; C. R. Geyer, D. Sen, Chem. Biol. 1997, 4, 579–593; S. W. Santoro, J. G. F., Proc. Natl. Acad. Sci. U.S.A. 1997, 94, 4262–4266; P. Burgstaller, M. Famulok, Angew. Chem. 1995,107, 1303–06; Angew. Chem. Int. Ed. Engl. 1995, 34, 1189–92; D. Faulhammer, M. Famulok, Angew. Chem. 1996, 108, 2984–88; Angew. Chem. Int. Ed. Engl. 1996,35,2837–2841; D. Faulhammer, M. Famulok, J. Mol. Biol. 1997, 269, 188–202; Y. Li, D. Sen, Nat. Struct. Biol. 1996, 3, 743–747; J. Burmeister, G. von Kiedrowski, A. D. Ellington, Angew. Chem. 1997, 109, 1379–81; Angew. Chem. Int. Ed. Engl. 1997, 36, 1321–1324; N. Carmi, L. A. Shultz, R. R. Breaker, Chem. Biol. 1996, 3, 1039–1046; N. Carmi, H. R. Balkhi, R. R. Breaker, Proc. Natl. Acad. Sci. U.S.A. 1998, 95, 2233–2237).

The catalytic and mechanistic scope of nucleic acids is limited since the natural nucleotide monomers possess minimal functionality compared to the repertoire available to Nature's dominant catalytic biopolymers, proteins. In recognition of this shortcoming, much attention has been focused on the development of functionalized nucleotides suitable for in vitro selection with the hope of increasing the potential of nucleic acids for binding and catalysis (B. E. Eaton, W. A. Pieken, Annu. Rev. Biochem. 1995, 64, 837–63; B. E. Eaton, Curr. Opin. Chem. Biol. 1997, 1, 10–16; G. J. Crouch, B. E. Eaton, Nucleosides Nucleotides 1994, 13 939–44; T. M. Dewey, A. Mundt, G. J. Crouch, M. C. Zyzniewski, B. E. Eaton, J. Am. Chem. Soc. 1995, 117, 8474–5; T. M. Dewey, M. C. Zyzniewski, B. E. Eaton, Nucleosides Nucleotides 1996, 15, 1611–1617; C. Tu, C. Keane, B. E. Eaton, Nucleosides Nucleotides 1995, 14, 1631–8; P. A. Limbach, P. F. Crain, J. A. McCloskey, Nucleic Acids Res. 1994, 22, 2183–96; H. Aurup, D. M. Williams, F. Eckstein, Biochemistry 1992, 31, 9636–41). Functionalized nucleotide triphosphates have been shown to be substrates for RNA polymerases (T. M. Dewey, A. Mundt, G. J. Crouch, M. C. Zyzniewski, B. E. Eaton, J. Am. Chem. Soc. 1995,117,8474–5; H. Aurup, D. M. Williams, F. Eckstein, Biochemistry 1992, 31, 9636–41).and catalytic RNA's dependent on the modified base for their activity have been selected (T. W. Wiegand, R. C. Janssen, B. E. Eaton, Chem. Biol. 1997, 4, 675–683; T. M. Tarasow, S. L. Tarasow, B. E. Eaton, Nature (London) 1997, 389, 54–57). Like RNA, DNA has also been selected to bind proteins and small molecules and more recently to catalyze reactions (S. E. Osborne, A. D. Ellington, Chem. Rev. (Washington, D.C.) 1997, 97, 349–370; M. Famulok, J. W. Szostak, Angew. Chem. 1992,104, 1001–11;Angew. Chem. Int. Ed. Engl. 1992, 31, 979–88; L. Gold, B. Polisky, 0. Uhlenbeck, M. Yarus, Annu. Rev. Biochem. 1995, 64, 763–97; R. R. Breaker, Chem. Rev. (Washington, D.C.) 1997, 97, 371–390; R. R. Breaker, Curr. Opin. Chem. Biol. 1997, 1, 26–31; J. R. Lorsch, J. W. Szostak, Acc. Chem. Res. 1996, 29, 103–10; R. R. Breaker, G. F. Joyce, Chem. Biol. 1994, 1, 223–9; B. Cuenoud, J. W. Szostak, Nature (London) 1995, 375, 611–14; R. R. Breaker, G. F. Joyce, Chem. Biol. 1995, 2, 655–60; C. R. Geyer, D. Sen, Chem. Biol. 1997, 4, 579–593; S. W. Santoro, J. G. F., Proc. Natl. Acad. Sci. U.S.A. 1997, 94, 4262–4266; P. Burgstaller, 3M. Famulok, Angew. Chem. 1995,107,1303–06; Angew. Chem. Int. Ed. Engl. 1995, 34, 1189–92; D. Faulhammer, M. Famulok, Angew. Chem. 1996, 108, 2984–88; Angew. Chem. Int. Ed. Engl. 1996, 35,2837–2841; D. Faulhammer, M. Famulok, J Mol Biol. 1997, 269, 188–202; Y. Li, D. Sen, Nat. Struct. Biol. 1996, 3, 743–747; J. Burmeister, G. von Kiedrowski, A. D. Ellington, Angew. Chem. 1997, 109, 1379–81; Angew. Chem. Int. Ed. Engl. 1997, 36, 1321–1324; N. Carmi, L. A. Shultz, R. R. Breaker, Chem. Biol. 1996, 3, 103 9–1046; N. Carmi, H. R. Balkhi, R. R. Breaker, Proc. Natl. Acad. Sci. U.S.A. 1998, 95, 2233–2237).

While DNA possesses enhanced stability as compared to RNA, the lack of a 2'-hydroxyl group which provides for the enhanced stability of this molecule further reduces the functionality available to this molecule for chemistry. In contrast to the success achieved in identifying modified nucleotide triphosphates for RNA libraries, there is but a single example of a deoxynucleotide triphosphate, 5-(1-pentynyl)-2' deoxyuridine triphosphate, that has been demonstrated to be a good substrate for a thermostable DNA polymerase and utilized in an in vitro DNA selection study (J. A. Latham, R. Johnson, J. J. Toole, Nucleic Acids Res. 1994, 22, 2817–22). Indeed, difficulties in identifying modified deoxynucleotide triphosphates substrates for the thermostable polymerases required for PCR have led recently to the development of novel strategies for in vitro selection without enzymatic amplification (J. Smith, E. V. Anslyn, Angew. Chem. 1997, 109, 1956–58; Angew. Chem. Int. Ed. Engl. 1997, 36, 1879–1881). These authors state that when modified oligomers are incorporated, the selection procedure is terminated after just one round of amplification since polymerases will not tolerate most modified mononucleotides. Therefore, the major impediment to the creation of novel functionally modified DNA catalysts and binding molecules is the determination of the substrate structures accepted by the thermostable polymerases.

The present invention provides a solution to this problem through the systematic synthesis of pyrimidine derivatives suitable for in vitro selections of modified DNAs.

BRIEF SUMMARY OF THE INVENTION

In one aspect, the present invention provides a modified pyrimidine nucleotide of the structure, below wherein X is NH$_2$ or =O, where when X is NH$_2$, (H) is absent and - - - is a chemical bond and when X is =O, - - - is absent and (H) is a hydrogen bonded to N-1, and C:C represents a carbon-carbon double bond or a carbon-carbon triple bond. In a preferred embodiment, C:C is a carbon-carbon double bond. Each R is independently a cation or wherein each R' is independently absent or a cation and m is 1, 2 or 3. The cation of R and R' is preferably a monovalent cation such as hydrogen or an alkali metal such as sodium (Na), potassium (K) or lithium (Li). Preferably, only one R is a cation. Thus, a compound of Structure II is preferably a 2'-deoxy-3'- or 5'-phosphate (mono-, di-, or tri-phosphate).

R$_1$ of Structure II is a functional group that mimics the structure and function of a naturally occurring amino acid residue. The functional group is preferably an amine or a carboxyl group. In accordance with this embodiment, R$_1$ is preferably where R$_2$ is R$_3$ is and n is an integer from 0 to 6. Preferably n is 0, 1 or 2.

In another aspect, the present invention provides a DNA molecule comprising one or more compounds of Structure II. Where the DNA molecule contains more than one such compound, each compound can be the same or different. In a related aspect, the present invention further provides a process of making a DNA molecule that contains a compound of Structure II comprising reacting the compound with other nucleotides together with a polymerase or reverse transcriptase enzyme under conditions sufficient for formation of the DNA.

A DNA molecule that contains one or more compounds of Structure II is more resistant to nuclease digestion than native DNA. Thus, in another aspect, the present invention provides a process of making a nuclease stable DNA molecule comprising inserting a modified nucleotide of this invention into the DNA molecule.

BRIEF DESCRIPTION OF THE DRAWINGS

In the drawings that form a portion of the specification

DETAILED DESCRIPTION OF THE INVENTION

1. The Invention

The present invention provides modified pyrimidines, nucleosides and nucleotides containing the modified pyrimidines, DNA molecules incorporating such modified nucleotides, uses of such DNA molecules as well as processes for making the nucleotides and DNA molecules.

II Modified Pyrimidines

Figure 1A:
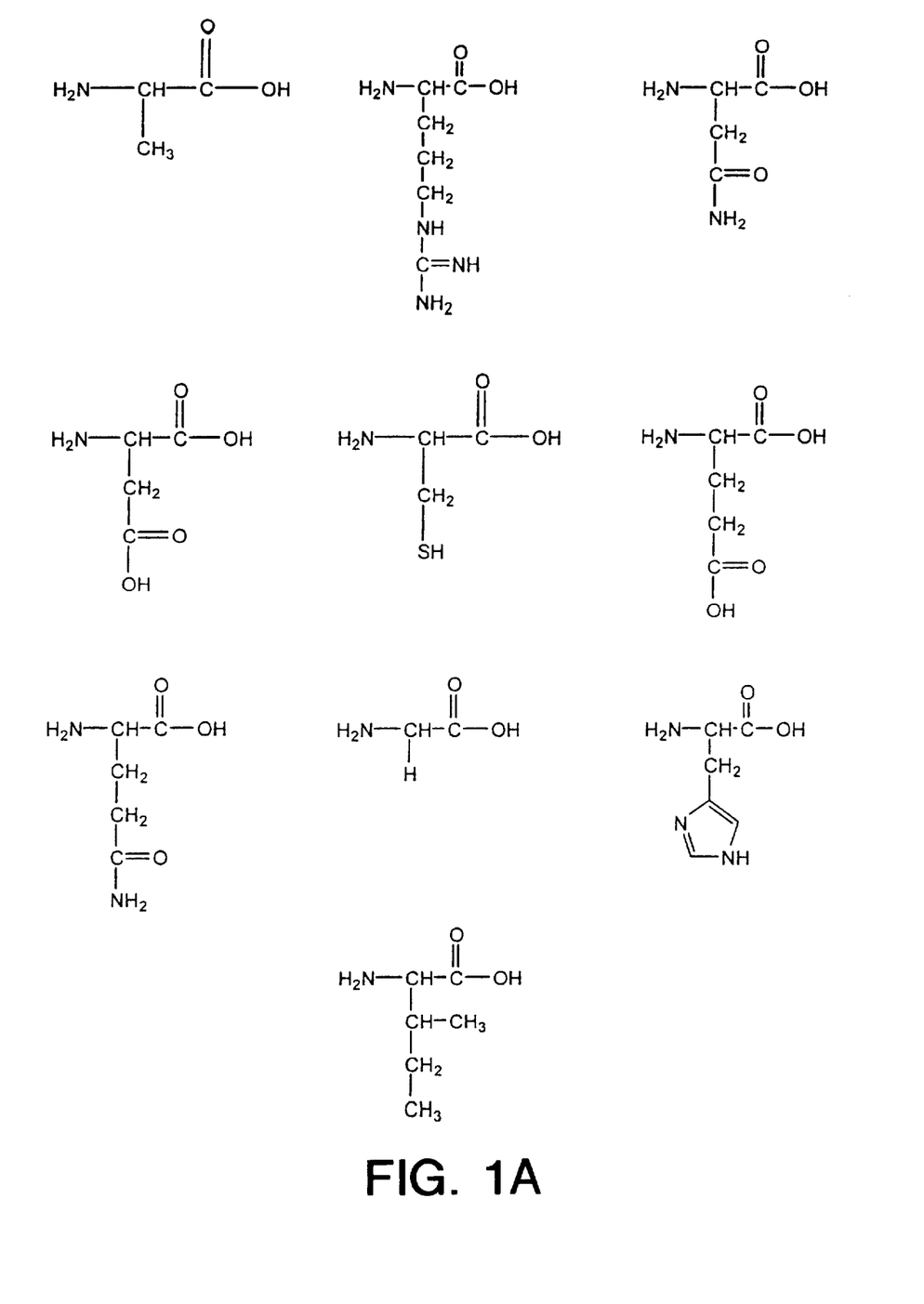
FIGS. 1A and 1B show the structure of the twenty naturally occurring amino acid residues.
Figure 1B:
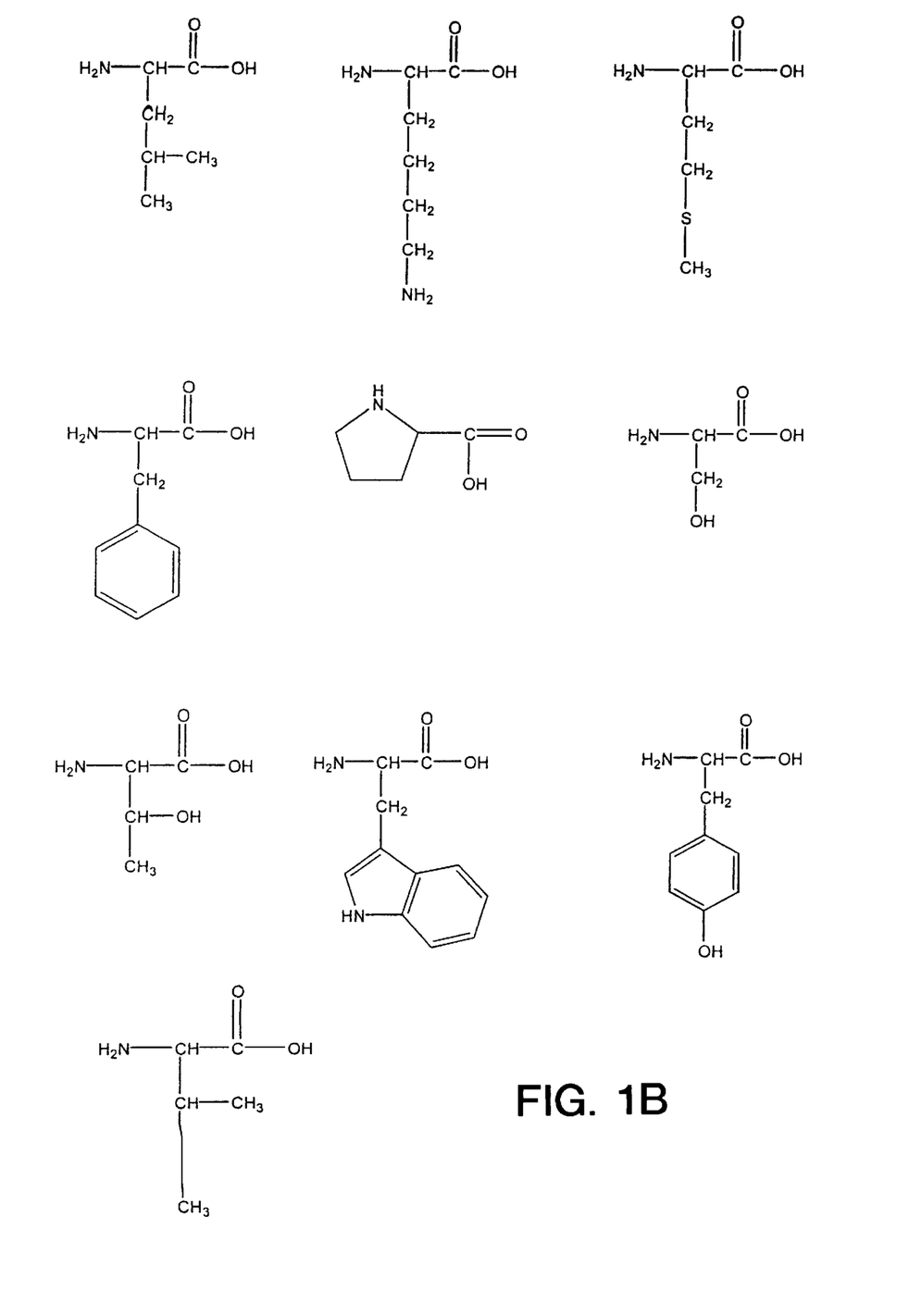

A pyrimidine is modified at the C5-position. More particularly, the C5-position is derivatized to contain a side chain. The side chain at the C5-position is designed and prepared to mimic the chemical and biological properties of an amino acid residue. FIG. 1 shows the structure of the twenty naturally occurring amino acid residues. In a preferred embodiment, the side chain mimics the properties of a polar amino acid residue. Thus, it is preferred that the side chain on the pyrimidine imparts a positive or negative charge onto the base.

In accordance with this embodiment, a nucleotide containing the modified base, when incorporated into a DNA molecule, imparts an electrostatic charge into the DNA. The functional groups of the natural nucleic acids have pK$_a$'s far removed from neutral pH and are therefore not suited for general acid-base catalysis in this pH range. Use of the modified nucleotides described herein provides potential for covalent, electrostatic, and an expanded potential for metal ion catalysis. This charge enhances the aptameric nature of the DNA (i.e., ability of DNA to interact with and bind polypeptides). The amino acid residue functional group is appended to the C5 position of the pyrimidine by means of a linker moiety. The linker moiety is an unsaturated hydrocarbon chain that includes an amide bond and a ketone group. A linker moiety shown to be suitable for linking a pyrimidine to functional groups has the structure shown below.

where Pyr is pyrimidine, $R_1$ is a functional group and C:C represents a carbon-carbon double bond or a carbon-carbon triple bond. In a preferred embodiment, C:C is a carbon-carbon double bond. Thus, a modified pyrimidine of the present invention has the structure I, shown below where X is NH2 or O, C:C is an unsaturated carbon bond and $R_1$ is wherein $R_2$ is wherein $R_3$ is and n is an integer from 0 to 6. Preferably n is 0, 1 or 2.

II Deoxyuridine Nucleosides and Nucleotides

Nucleosides and nucleotides of the present invention contain the modified pyrimidine as set forth above in Structure I. In addition, the modified nucleosides and nucleotides comprise a ribose sugar. The ribose can be hydroxylated or non-hydroxylated at the 2'-position. In a preferred embodiment, the hydroxyl group at the 2'-position of the ribose is lacking and the sugar moiety is a dexoyribose. In accordance with this preferred embodiment, a modified nucleoside/nucleotide of this invention has the structure II, below where X, C:C and $R_1$ are as defined above with regard to Structure I and each R is independently a cation or wherein each R' is independently absent or a cation and m is 1, 2, or 3. The cation of R and R' is preferably a monovalent cation such as hydrogen or an alkali metal salt such as sodium (Na), potassium (K) or lithium (Li).

Figure 2:
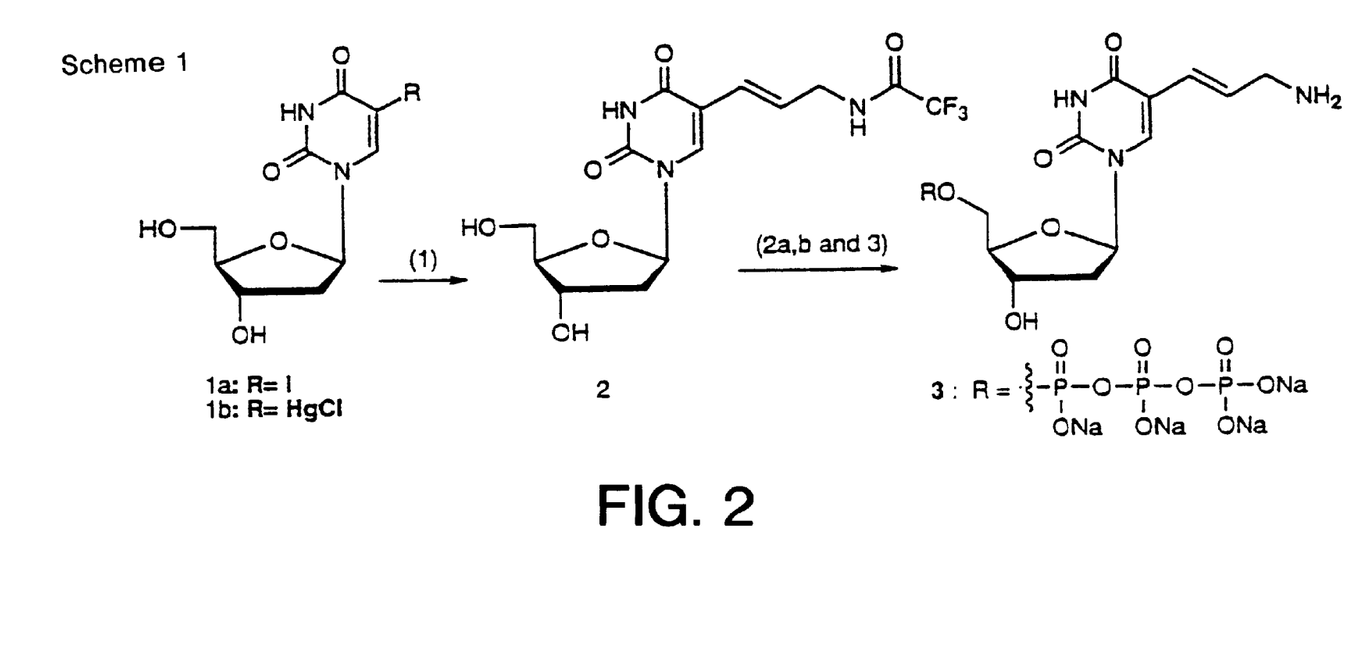
FIG. 2 shows a synthetic scheme for making a nucleotide triphosphate precursor

A modified nucleotide of the present invention can be made using a variety of synthetic procedures (See Scheme 1, FIG. 2). A synthetic process begins with the synthesis of C-5(3-aminopropenyl)- 2' deoxyuridine triphosphate or C-5 (3-aminopropenyl)- 2' deoxycytosine triphosphate from known compounds. Scheme 1, FIG. 2 shows the synthesis of C-5(3-aminopropenyl)- 2' deoxyuridine triphosphate from known compound 2. A palladium catalyzed route starting from commercially available 5-iododeoxyuridine was found to be preferable to the earlier synthetic scheme of Cook et al. (A. F. Cook, E. Vuocolo, C. L. Brakel, *Nucleic Acids Res.* 1988, 16, 4077–95) starting with 5-chloromercuri-2' deoxyuridine, though both provided 2 in similar yields. Optimization of the synthesis of 2 and its conversion to the corresponding 5'-triphosphate using the methodology of Kovacs and Ötvös (T. Kovacs, L. Otvos, *Tetrahedron Lett.* 1988, 29, 4525–8.) followed by deprotection of the amine provided 3 isolated on a 100 mg scale with analytical purity. Compound 3 was synthesized previously from deoxyuridine triphosphate (dUTP), however, problems with contaminating byproducts and the expense of dUTP as a starting material posed serious obstacles for this synthetic route (P. R. Langer, A. A. Waldrop, D. C. Ward, *Proc. Natl. Acad. Sci. U.S.A.* 1981, 78, 6633–7). A detailed description of the synthesis of Compounds 2 and 3 can be found hereinafter in the Examples. Compound 3 was then used as the starting material for preparation of modified deoxyuridine nucleotides using standard techniques well known in the art. Those modified deoxyuridine nucleotides are shown in Scheme 2, FIG. 3. Detailed descriptions of the preparation of numerous modified nucleotides can be found hereinafter in the Examples.

IV DNA Molecules containing Modified Nucleotides

In a related aspect, the present invention provides a DNA molecule that comprises a modified nucleotide as set forth above. The DNA molecule can contain a plurality of modified nucleotides. A DNA molecule of this invention can be a single stranded or double stranded molecule. Where the DNA molecule is double stranded, the modified nucleotide (s) can be included in one or both strands.

A DNA molecule of this invention can be of any length. Preferably, a DNA molecule contains less than about 2,000 base pairs and, more preferably less than about 1,000 base pairs. Even more preferably, a DNA molecule contains less than about 500 base pairs. In an especially preferred embodiment, a DNA molecule contains less than about 100 base pairs.

A DNA molecule of this invention has many uses. The DNA molecule can be genomic DNA and direct transcription of RNA molecules encoding specific polypeptides. The DNA molecule can be a cDNA molecule in an expression vector that directs expression of a specific polypeptide. The DNA molecule can be used as a hybridization probe that binds to complementary DNA molecules. The DNA molecule can be an antisense DNA molecule used to inhibit expression. The DNA molecule can also be used as a primer to direct the synthesis of other DNA molecules.

A DNA molecule of this invention can be a hybridization probe designed and synthesized to anneal with a target polynucleotide sequence to form a nucleic acid duplex. Time, temperature and pH conditions required to accomplish hybridization depend, as is well known in the art, on the length of the probe to be hybridized, the degree of complementarity between the probe and the target, the guanidine and cytosine content of the probe, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Hybridization can be carried out in a homogeneous or heterogeneous format as is well known. The homogeneous hybridization reaction occurs entirely in solution in which both the probe and the nucleic acid sequences to be hybridized (target) are present in soluble forms in solution. A heterogeneous reaction involves the use of a matrix that is insoluble in the reaction medium to which either the probe or target nucleic acid is bound. Where the nucleic acid containing a target sequence is in a double-stranded form, it is preferred to first denature the nucleic acid, as by heating or alkali treatment, prior to conducting the hybridization reaction. The denaturation of the nucleic acid can be carried out prior to admixture with a probe to be hybridized, or can be carried out after the admixture of the nucleic acid with the probe.

Effective amounts of the probe present in the hybridization reaction admixture are generally well known and are typically expressed in terms of molar ratios between the probe to be hybridized and the template. Preferred ratios are hybridization reaction mixtures containing equimolar amounts of the target sequence and the probe. As is well known, deviations from equal molarity will produce hybridization reaction products, although at lower efficiency. Thus, although ratios where one component can be in as much as 100-fold molar excess relative to the other component, excesses of less than 50-fold, preferably less than 10-fold, and more preferably less the 2-fold are desirable in practicing the invention.

The probe can include a label or indicating group that will render the duplex detectable. Typically such labels include radioactive atoms, chemically modified nucleotide bases, and the like. The probe can be labeled, i.e., operatively linked to an indicating means or group, and used to detect the presence of a specific nucleotide sequence in a target template.

Radioactive elements operatively linked to or present as part of an probe (labeled oligonucleotide) provide a useful means to facilitate the detection of a duplex. A typical radioactive element is one that produces beta ray emissions. Elements that emit beta rays, such as $^3H$, $^{12}C$, $^{32}P$ and $^{35}S$ represent a class of beta ray emission-producing radioactive element labels. A radioactive probe is typically prepared by enzymatic incorporation of radioactively labeled nucleotides into a nucleic acid using kinase. Alternatives to radioactively labeled oligonucleotides are oligonucleotides that are chemically modified to contain metal complexing agents, biotin-containing groups, fluorescent compounds, and the like. One useful metal complexing agent is a lanthanide chelate formed by a lanthanide and an aromatic beta-diketone, the lanthanide being bound to the nucleic acid or probe via a chelate forming compound such as an EDTA-analogue so that a fluorescent lanthanide complex is formed. See U.S. Pat. Nos. 4,374,120, 4,569,790 and published Patent Application Nos. EP0139675 and W087/02708. Biotin or acridine ester-labeled oligonucleotides and their use to label polynucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled probe present in a duplex renders the duplex itself labeled and therefore distinguishable over other nucleic acids present in a sample to be assayed. Detecting the presence of the label in the probe, and thereby the presence of the duplex, typically involves separating the duplex from any labeled probe that is not hybridized to a duplex. Techniques for the separation of single stranded oligonucleotide, such as a non-hybridized, labeled probe from duplex are well known and typically involve the separation of single stranded from double stranded nucleic acids on the basis of their chemical properties. More often separation techniques involve the use of a heterogeneous hybridization format in which the non-hybridized probe is separated, typically by washing, from the duplex that is bound to an insoluble matrix. Exemplary is the Southern blot technique, in which the matrix is a nitrocellulose sheet and the label is $^{32}P$ (Southern, *J. Mol. Biol.,* 98:503, 1975).

The probes can also be advantageously linked, typically at or near their 5'-terminus, to a solid matrix, i.e., aqueous insoluble solid support. Useful solid matrices are well known in the art and include cross-linked dextran such as that available under the tradename SEPHADEX from Pharmacia Fine Chemicals (Piscataway, N.J.); agarose, polystyrene or latex beads about 1 micron to about 5 mm in diameter, polyvinyl chloride, polystyrene, cross-linked polyacrylamide, nitrocellulose or nylon-based webs such as sheets, strips, paddles, plates microtiter plate wells and the like. It is also possible to add "linking" nucleotides to the 5' or 3' end of the member probe, and use the linking probe to operatively link the member to the solid support.

In nucleotide hybridizing assays, the hybridization reaction mixture is maintained in the contemplated method under hybridizing conditions for a time period sufficient for the probes having complementarity to the predetermined sequence on the template to hybridize to complementary nucleic acid sequences present in the template to form a hybridization product, i.e., a complex containing probe and target nucleic acid.

A probe of this invention contains less than about 50 nucleotides and, preferably less than about 25 nucleotides.

The probe contains more than about 5 nucleotides. In a preferred embodiment, the probe contains more than about 10 nucleotides and, more preferably greater than about 15 nucleotides.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on may factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.*, 12:7057–70 (1984); Studier et al., *J. Mol. Biol.*, 189:113–130 (1986); and *Molecular Cloning: A Laboratory Manual Second Edition*, Maniatis et al., eds., Cold Spring Harbor, N.Y. (1989). When a primer containing a DNA-dependent RNA polymerase promoter is used the primer is hybridized to the polynucleotide strand to be amplified and the second polynucleotide strand of the DNA-dependent RNA polymerase promoter is completed using an inducing agent such as E. coli DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197–1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719–736 (1974).

The polynucleotide primers can be prepared using any suitable method, such as, for example, the phosphotriester or phosphodiester methods see Narang et al., *Meth. Enzymol.*, 68:90, (1979); U.S. Pat. No. 4,356,270; and Brown et al., *Meth. Enzymol.*, 68:109, (1979).

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

A DNA molecule containing a modified nucleotide as set forth above can be made using standard procedures well known in the art such as solid phase phosphoramidite chemistry. All that is needed is to use a modified nucleotide of this invention in the synthetic scheme. A modified nucleotide of this invention can also be incorporated into a DNA molecule using enzymes such as polymerases and reverse transcriptases. A reaction mixture for making a DNA molecule comprises one or more modified nucleotides of this invention together with dATP, dGTP, dTTP and dCTP. The modified nucleotides can be in addition to or replace dTTP and /or dCTP.

By way of example, Compound 3 from Scheme 1., FIG. 2, acted as a substrate in place of deoxythymidine triphosphate, dTTP, for thermostable DNA polymerases using typical PCR conditions. Commercially available thermostable DNA polymerases from five organisms were studied; Taq from Thermus aquaticus, Vent from Thermococcus litoralis, Pfu from Pyrococcus furiosus, and rTh from Thermus thermophilus. PCR assays with compound 3 demonstrated its incorporation into the 519 base pair product only with rTh polymerase. Several derivatives of 3 have been shown to be substrates for *E. coli* DNA polymerase and useful in nick translation and random primed synthesis when they replace dTTP. Homogeneous incorporation of these derivatives in PCR is not possible due to chain termination, see 11c for discussion of derivatives in PCR: a) M. Shimkus, J. Levy, T. Herman, *Proc. Natl. Acad. Sci. U.S.A.* 1985, 82, 2593–7; b) B. L. Iverson, P. B. Dervan, *J Am. Chem. Soc.* 1987, 109, 1241–3. and ref. 10; c) H. Yu, J. Chao, D. Patek, R. Mujumdar, A. S. Waggoner, *Nucleic Acids Res.* 1994, 22, 3226–32. Successful PCR with this template requires incorporation of 246 modified bases including a single stretch of 8 contiguous thymidines.

Figure 3:
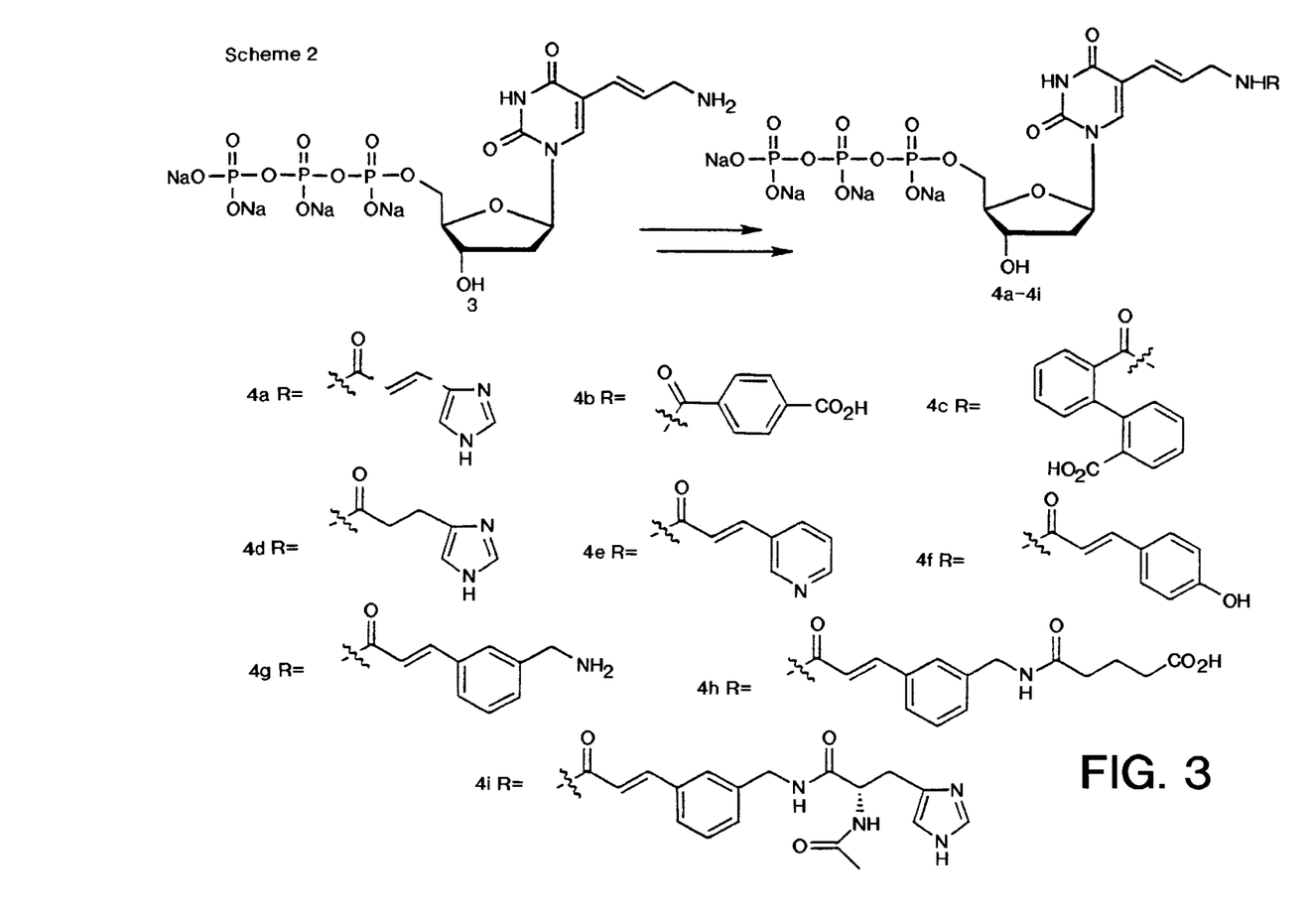
FIG. 3 shows a generalized synthetic scheme for making modified deoxyuridines.

Compound 3 was derivatized with three different N-hydroxysuccinimide esters to prepare Compounds 4a–c (Scheme 2 FIG. 3). Compound 4a, an 4-imidazole acrylic acid derivative, proved to be an excellent substrate for all the polymerases tested producing an amount of PCR product similar to that obtained with dTTP. Further study of substrates 4b and 4c with variation of $Mg^{+2}$ (15 to 30 mM) and analog concentrations (200 to 800 mM) failed to define conditions that allowed for incorporation of these modified bases. To study the structural feature of 4a that allowed for it to be recognized as a good substrate for the polymerases, Compound 4d, a reduced analog of 4a, was synthesized. No conditions could be defined with any of the polymerases that allowed for PCR with 4d suggesting that the rigid and extended a,b-unsaturated arm of the 4-imidazole acrylic acid provided for its activity. To test this structure-activity relationship, 4e–4g maintaining the a,b-unsaturated linker arm common to 4a, were also prepared (Scheme 2, FIG. 3). Compounds 4e–4g were substrates for all the polymerases tested. Compound 4g, with a free amino group, was used as a template for the synthesis of Compounds 4h and 4i. Analog 4h was a good substrate for all thermostable polymerases tested while 4i was a substrate only for rTh polymerase.

Evidence that the modified products is dUTP's are indeed incorporated into the PCR products is provided in the substantial mobility shift obtained for the modified DNA products that is indicative of both the mass increase associated with the modified base as well as the charge of the DNA product. DNA incorporating analog 4g, which should possess of full positive charge at neutral pH, migrated slower than DNA incorporating 4h that has an increased mass and negative charge at neutral pH. The role of the extended linker arm is apparent in comparing the efficiency of incorporation of 3 with 4g, were both carry a primary amine. The larger derivative 4g bears the extended linker arm and is a robust substrate for PCR as compared to 3.

Reverse transcriptases may also be utilized in conjunction with PCR in in vitro selection schemes of DNA enzymes. We tested the ability of Compounds 3 and 4a–i to act as substrates of Superscript II reverse transcriptase (Gibco/BRL) and determined that all but 4c and 4h were substrates in template directed synthesis assays (see Example 3). The specificity of this reverse transcriptase is broader and not predictive of the structural requirements of the thermostable polymerases.

PCR products obtained using modified dUTP's were cloned and sequenced. PCR products incorporating modified nucleotide analogs were cloned into the vector pCR2.1TOPO using the topoisomerase-activated vector provided from the manufacturer (Invitrogen). The fidelity of incorporation of the modified dUTP's was indistinguishable from that observed with dTTP incorporation in the control reactions. The key criteria for the use of a modified dNTP in an in vitro selection methodology is its ability to serve as a substrate for thermostable polymerases and the resulting product to serve as a template for multiple cycles of PCR amplification. These criteria were met with Compounds 3, 4a and 4e–i.

Analogs 4g and 4h provide for the first examples of the incorporation of cationic and anionic nucleotide analogs into DNA by PCR, dramatically altering its electrostatic properties. With the exception of 4e, the analogs may be regarded as functional equivalents of the amino acids lysine, 3 and 4g; histidine, 4a and 4i; tyrosine, 4f; and aspartic and glutamic acid, 4h. The successful incorporation of L-histidine in analog 4i supports the possibility of incorporation of other natural amino acids as well as small peptides. All the analogs provide new potential for hydrophobic binding interactions that are essential for folding and pocket formation in protein enzymes as well as for $pK_a$ perturbations of functional groups.

In another aspect, the present invention provides a process for increasing the resistance of a DNA molecule to nuclease digestion. The process comprises the step of replacing one or more pyrimidine nucleotides in the DNA molecule with a modified nucleotide of this invention. The greater the number of substitutions, the greater the resistance of the resulting DNA molecule to nuclease digestion. It is preferred, therefore, that all thymidines and cytosines are replaced with the modified deoxyuridines and deoxycytosines. PCR products incorporating modified bases were found to be resistant to cleavage by the restriction enzymes Sac I and Xba I that recognize the sequences GAGCTC and TCTAGA, respectively, and cleave the natural DNA product.

Replacement of one or more bases in a DNA molecule with a modified nucleotide can be accomplished using a number of standard techniques well known in the art. As disclosed hereinbefore, solid phase synthetic procedures can be used to construct a de nova molecule that incorporates the modified nucleotide. Because the modified nucleotides of this invention are compatible with a variety of polymerases and reverse transcriptases, DNA molecules of a defined sequence can also be prepared using such enzymes.

Substitutions can also be made in DNA molecules using techniques known collectively in the art as site directed mutagenesis (See. e.g., *Current Protocols in Molecular Biology*, Ed. By Ausabel et al., John Wiley and Sons, Inc., 1998; *Molecular Cloning: A Laboratory Manual*, Sambrook, Fritsch and Maniatis, Cold Spring harbor Laboratory Press, 1989, the disclosures of which are incorporated herein by reference). Such mutagenesis techniques have been used to make substitutions in DNA molecules to alter the expression product of such molecules (See e.g., U.S. Pat. Nos. 5,543,302 and 5,550,042). Although the technique of site directed mutagenesis can be employed as described, other mutagenic protocols such as cassette mutagenesis and localized random mutagenesis can also be used.

The Examples that follow illustrate preferred embodiments of the present invention and are not limiting of the specification and claims in any way.

EXAMPLE 1

Synthesis of 5-(3-trifluroacetylaminopropenyl) -2'-deoxyuridine (Compound 2)

5-(3-Trifluroacetylaminopropenyl)-2'-deoxyuridine 2 was first synthesized by Cook and his coworkers[8] from 5-chloromercuri-2'-deoxyuridine 1b. We synthesized 2 from commercially available 5-iodo-$2'$-deoxyuridine using a similar procedure. A suspension of 5-iodo-$2'$-deoxyuridine 1a (3.5 g, 10 mmol) in sodium acetate buffer (0.1 M, pH 5.2 ) was treated with trifluroacetyl allylamide (13 g, 88 mmol) followed by a solution of sodium tetrachloropalladate (2.5 g in 5 ml water ). The mixture was stirred at rt for 18 hrs and then filtered through celite. The filtrate was concentrated and extracted several times with ethyl acetate. The combined organic layers were dried over anhydrous magnesium sulfate. The solvent was evaporated to dryness and the product purified by column chromatography on silica gel using ethyl acetate as eluent, 1.7 g (44 %) of deoxyuridine derivative 2 was obtained. $^1$H-NMR (CD$_3$OD): 8.11 (s, br, 1H) C-6 H; 6.45 (m, 1H) and 6.16 (m, 2H) vinylic protons and H-1'; 4.32 (m, 1H) H-3'; 3.8, (m, 3H) allylic CH$_2$ and H-4'; 3.75–3.60 (m, 2H) CH$_2$-5',5"; 2.17 (m, 2H) H-2',2".

EXAMPLE 2

Synthesis of C-5(3-aminopropenyl)-2'-deoxvuridinetriphosphate (Compound 3)

Allylamine-deoxyuridine 2 (126 mg, 0.33 mmol) was stirred in dry trimethylphosphate (0.75 ml) with proton sponge (100 mg, 0.47 mmol) at 0° C. Phosphorous oxychloride (99.9% Aldrich, 35 1) was added and the mixture was stirred at 0–4 C. After 2.5 hrs, a solution of tri-n-butylammonium pyrophosphate in anhydrous DMF (0.5 M, 3 ml) and n-tributylamine (0.3 ml) was quickly added to the reaction mixture at 0 C. After 1 min, an aqueous solution of triethylammonium bicarbonate (0.2 M) was poured into the mixture. After evaporation, the residue was treated with aqueous ammonia (2 ml), and stirred overnight at rt. After evaporation of the ammonia, the residue was purified on DEAE-Sephadex A-25 column chromatography using triethylammonium bicarbonate buffer (0.2–0.5 M, pH 7.5 ). The final purification was achieved by reverse phase HPLC using the gradient 0–3% acetonitrile in 50 mM triethylammoniumbicarbonate buffer over 3 0 min to give 110 mg (54%) of triphosphate 3. $^1$H-NMR (D$_2$O): 8.17 (s, br, 1H) C-6 H; 6.58–6.54 (d, 1H) and 6.48–6.40 (m, 1H) ,6.35 (t, 1H) vinylic protons and H-1'; 4.66 (m, 1H) H-3'; 4.26–4.2 (m, 3H) 5', 5" CH$_2$ and H-4'; 3.70 (d, 2H) allylic CH$_2$; 2.41 (m, 2H) H-2',2". $^{13}$C-NMR (D$_2$O): 166.67; 153.35; 141.0; 128.74; 124.7; 114.00; 88.27; 87.90; 72.7; 67.66; 43.60; 41.98. $^{31}$P-NMR (D$_2$O): -9.42 (d); -10.73 (d); -21.38 (t). MS (Electrospray): m/z 589 [M+H$^+$]; 611 [M+Na$^+$]; 633. [M+2Na$^+$2H$^+$]. Anal. calcd for C$_{12}$H$_{16}$N$_3$Na$_4$O$_{14}$P$_3$: C, 23.58; H, 2.64; N, 6.88. Found: C, 23.75; H, 2.81; N,7.00

EXAMPLE 3

General synthesis of modified dUTPs 4a, 4d, 4e, and 4f

Allylamine- dUTP 3 (30 mg, 50 mol) was treated with a slight excess of the corresponding N-hydroxysuccinimide ester in 0.1 M sodium borate buffer and DMF (1:1) at rt and stirred for 10–20 hrs. After completion of the reaction (as monitored on TLC using ammonia, water and isopropanol, 2:1:1), the mixture was evaporated to dryness. The triphosphates were purified by reverse phase HPLC. $^1$H nuclear magnetic resonance ($^1$H-NMR) spectra were recorded on a Fourier Transform 400-MHz, (100-MHz for $^{13}$C-NMR, 161.9 MHz for $^{31}$P-NMR) spectrometer and are reported in parts per million (ppm). All modified dUTPs were purified using preparative RP-HPLC; Waters PrepPak 500 column, C-18, 300 Å poresize, 15 mm particle size, 4.7 ×30 cm, flow rate 80 ml/min. For all modified dUTPs, the triethylammonium counterion was converted to the sodium ion using the standard procedure.

Modified dUTP 4a: 26 mg (73%). $^1$H-NMR D$_2$O): (7.94 (s, br, 1H) H-6; 7.86 (s, br, 1H) and 7.42 (m, 2H), 6.6 (d, 1H) imidazole-H and vinylic protons; 6.44 (m, 1H) and 6.35–6.30 (m, 2H) allylamine vinylic protons and H-1'; 4.64 (s, br, 1H) H-3'; 4.20–4.19 (d, br, 3H) 5', 5"CH$_2$ and H-4'; 4.01 (d, 2H) allylic CH$_2$; 2.38 (m, 2H) H-2',2". $^{13}$C-NMR (D$_2$O) : (170.75; 166.45; 153.09; 140.25; 133.16; 129.75; 124.52; 114.57; 114.50; 87.96; 87.83; 87.75; 73.08; 72.78; 67.88; 44.19; 41.07; 32.70. $^{31}$P-NMR (D$_2$O): (-0.36 (d); -10.94 (d); -21.43(t). MS (Electrospray): m/z 709 [M+H$^+$]; 731 [M+Na$^+$]; 753 [M+2Na$^+$-H+]; 775 [M+3Na$^+$-2H$^+$]. Anal. calcd for C$_{18}$H$_{20}$N$_5$Na$_4$O$_{15}$P$_3$: C, 29.57; H, 2.76; N, 9.58. Found: C, 29.15; H, 2.85; N, 9.42

Modified dUTP 4d: 24 mg (67%). $^1$H-NMR (D$_2$O): (8.3(s,1H) imidazole; 7.93 (s, br, 1H) H-6; 7.1 (s, 1H) imidazole, 6.32 (m, 2H) and 6.15 (d, 1H) vinyl protons and H-1'; 4.64 (s, br, 1H) H-3'; 4.20–4.19 (d, br, 3H) 5', 5" CH$_2$ and H-4'; 3.8 (m, 2H) allylic CH$_2$; 2.99 (t, 2H) and 2.67 (t, 2H) 2 CH$_2$; 2.38 (m, 2H) H-2',2". $^{13}$C-NMR (D$_2$O): (182.0; 177.54; 176.0; 166.67; 153.35; 140.23; 129.93; 124.24; 114.88; 88.15; 88.06; 87.86; 73.2; 67.79; 51.26; 43.59; 41.35; 37.74.$^{31}$P-NMR (D$_2$O): (-0.45 (d); -11.00 (d); -21.92 (t). MS (Electrospray) : m/z 711 [M+H$^+$]; 733 [M+Na$^+$]; 755 [M+2Na$^+$-H$^+$]; 777 [M+Na$^+$-2H$^+$]; Anal. calcd for C$_{18}$H$_{22}$N$_5$Na$_4$O$_{15}$P$_3$:C, 29.48; H, 3.02; N, 9.55. Found: C, 29.80; H, 3.11; N, 9.63

Modified dUTP 4e: 24 mg (65%). $^1$H-NMR (D$_2$O): (8.7 (s, br, 1H), 8.47 (s, br, 1H), 8.12 (d, 1H) pyridyl; 7.93 (s, br, 1H) H-6; 7.43 (m, 2H) pyridyl and acrylyl-H, 6.79 (d, 16Hz, 1H) acrylyl-H; 6.48 (m, 1H) and 6.35–6.27 (m , 2H) allylamine vinylic protons and H-1'; 4.77 (s, br, 1H) H-3'; 4.22–4.18 (d, br, 3H) 5', 5" CH$_2$ and H-4'; 4.04 (s, br, 2H) allylic CH$_2$; 2.35 (m, 2H) H-2', 2". $^{13}$C-NMR (D$_2$O): (169.99; 166.56; 153.14; 140.42; 139.44; 138.05; 129.61; 125.02; 124.73; 114.57; 87.90; 87.91; 87.85; 72.77; 67.73; 44.24; 43.59; 41.11. $^{31}$P-NMR (D$_2$O): (-0.45 (d); -11.00 (d); -21.92 (t). Anal. calcd for C$_{18}$H$_{22}$N$_5$Na$_4$O$_{15}$P$_3$ H$_2$O: C, 31.60; H, 3.04; N 7.37. Found C, 31.95; H, 3.11; N, 7.78.

Modified dUTP 4f: 24 mg (62%). $^1$H-NMR (D$_2$O): (7.92 (s, 1H) H-6; 7.55 (d, br, 2H) phenyl; 7.46 (d, 16 Hz, 1H) vinyl-H, 6.89 (d, 1H ) phenyl; 6.55 (d, 16 Hz, 1H) vinyl-H; 6.5–6.28 (m, 3H) allylamine vinylic protons and H-1'; 4.64 (s, br, 1H) H-3'; 4.20–4.19 (d, br, 3H) 5', 5" CH$_2$ and H-4'; 4.01 (m, 2H) allylic CH$_2$; 2.38 (m,2H) H-2', 2". $^{13}$C-NMR (D$_2$O): (171.08; 166.44; 166.36; 160.13; 153.06; 143.25; 140.19; 132.35; 129.82; 128.96; 124.46; 119.58; 118.43; 114.57; 88.02; 87.82; 87.73; 73.08; 67.93; 44.22; 40.94. $^{31}$P-NMR (D$_2$O): (-0.45 (d); -1 1.00 (d); -21.92 (t). MS (Electrospray) : m/z 691 [M+Na$^+$]; 667 [M-H$^+$]. Anal. calcd for C$_{21}$H$_{22}$N$_3$Na$_4$O$_{16}$P$_3$: C, 33.31; H, 2.93 ; N, 5.55. Found: C, 33.67; H, 3.12; N, 5.21.

Modified dUTP 4b: Allylamine dUTP 3 (30 mg, 50 (mol) was reacted with monomethylterephthalic acid-N-hydroxysuccinimide ester (70 mg, 250 (mol) in 0.1 M sodium borate buffer and DMF (1: 1) at rt for 12 hrs and the resulting methyl ester was hydrolyzed by adding 1N sodium hydroxide to produce dUTP 4b. Excess sodium hydroxide was neutralized to pH 7 using IN HC1 at 0 (C. The reaction mixture was then evaporated to dryness and the residue was purified by reverse phase HPLC to give 22 mg (58 %) of dUTP 4b. $^1$H-NMR (D$_2$O): (7.90 (d, 2H) phenyl; 7.76 (s, br, 1H) H-6; 7.67 (d, 2H) phenyl; 6.23–6.14 (m, 3H) allylamine vinylic protons and H-1'; 4.46 (s, br, 1H) H-3'; 4.03 (s, br, 3H) 5', 5" CH$_2$ and H-4'; 3.95 (s, br, 2H) allylic CH$_2$; 2.2 (m, 2H) H-2',2". $^{31}$P-NMR (D$_2$O): (-0.36 (d); -10.94 (d); -21.43 (t). MS (FT-MALDI): 759.9685; C$_{20}$H$_{24}$N$_3$Na$_4$O$_{17}$P$_3$ (calcd. 759.6975); 781.9481 [M+Na$^+$, calcd. 781.9061].

Modified dUTP 4c: Allylamine-dUTP 3 (30 mg, 50 (mol) was reacted with biphenic anhydride (56 mg, 250 (mol) in 0.1 M sodium borate buffer and DMF (1:1) at rt and stirred for 12 hrs. After completion, the reaction mixture was evaporated to dryness and residue was purified by reverse phase HPLC to give 29 mg (71%) of 4c. $^1$H-NMR (D$_2$): (7.67 (s, 1H) H-6; 7.5-7.05 (m, 8H) biphenyl protons; 6.30 (t, 1H) H-1'; 5.9 (d, 1H) and 5.8 (m, 1H) allylamine vinylic protons; 4.63 (s, br, 1H) H-3'; 4.21 (s, br, 3H) 5', 5" CH$_2$ and H-4'; 3.9-3.3 (d, br, 2H) allylic amine CH$_2$; 2.42 (m, 2H) H-2',2". $^{31}$P-NMR (D$_2$O): (-0.36 (d); –10.94 (d); –21.43 (t). MS (FT-MALDI): 836.9997, C$_{26}$H$_{24}$N$_3$Na$_4$O$_{17}$P$_3$ (calcd. 834.9989).

Modified dUTP 4g: Allylamine-dUTP 3 (30 mg, 50 (mol) was reacted with -trifluroacetylamiomethyl-trans-cinnamic acid-N-hydroxysuccinimideester (100 mg, 250 (mol ) in 0.1 M sodium borate buffer and DMF (1: 1) at rt for 24 hrs. The resulting reaction mixture was evaporated to dryness. The residue was added to conc. ammonia (1 mL). The reaction mixture was evaporated to dryness and the residue was purified by reverse phase HPLC to give 23 mg (60%) of 4g. $^1$H-NMR (D$_2$O): (8.05 (s, 1H) H-6; 7.53–7.40 (m, 5H) phenyl and cinnamic vinyl- H; 6.98 (d, 16 Hz, 1H) cinnamic vinyl-H; 6.43–6.32 (m, 3 H) allylamine vinylic protons and H-1'; 4.71 (s, br, 1H) H-3'; 4.32–3.95 (m, 7H) 5', 5" CH$_2$, H-4", allylic CH$_2$, benzylic CH$_2$; 2.38 (m, 2H) H-2', 2". $^{13}$C-NMR (D$_2$O): (170.49; 167.11; 153.58; 142.39; 140.20; 137.55; 132.57; 132.02; 131.66; 129.47; 129.41; 124.59;

123.48; 114.64; 87.96; 87.87; 87.74; 72.51; 67.62; 45.15; 44.00; 41.22. $^{31}$P-NMR (D$_2$O): (-.5.36 (d); -10.9 (d); -21.16 (t). MS (Electrospray): m/z 683 [MH$^+$]; 705 [M+Na$^+$]; 727 [M+2Na$^+$-H$^+$]; 749 [M+3Na$^+$-2H$^+$]; 771 [M+4Na$^+$-3H$^+$].

Modified dUTP 4h: Benzylamine-dUTP 4g (38 mg, 50 (mol) was reacted with glutaric anhydride (57 mg, 0.5 mmol) in 0. I M sodium borate buffer and DMF (1: 1) at rt for 12 hrs. After the completion of the reaction, the mixture was evaporated to dryness and the residue was purified by reverse phase HPLC to give 26 mg (60%) of 4g. $^1$H-NMR (D$_2$O): (7.90 (s, 1H) H-6; 7.57–7.31 (m, 5H) phenyl and cinnamic vinyl- H; 6.68 (d, 16 Hz, 1H) cinnamic vinyl-H, 6.47–6.28 (m, 3H) allylamine vinylic protons and H-1'; 4.67 (s, br, 1H) H-3'; 4.37 (m, 2H), 4.22 (m, 3H) 5', 5"CH$_2$,H-4'; 4.01 (d, br, 2H) allylic CH$_2$; 2.39 (m, 2H), 2.29 (m, 2H), 2.19 (m, 2H), 1.83 (m, 2H) 3XCH$_2$ for glutaric acid and H-2',2". $^{13}$C-NMR(D$_2$O): (184.99; 178.82; 170.83; 153.94; 143.27; 141.10; 140.39; 137.16; 131.79; 131.23; 129.68; 129.5; 124.79; 122.85; 114.71; 87.95; 87.86; 87.71; 72.67; 67.69; 51.31; 45.21; 44.23; 40.98; 39.20; 37.91; 24.91. $^{31}$P-NMR (D$_2$O): (-.5.26 (d); -10.5 (d); -21.23 (t). MS (Electrospray): m/z 819 [M+Na$^+$]; 841 [M+2Na$^+$H$^+$]; 863 [M+3Na$^+$-2H$^+$]; 885 [M+4Na$^+$-3H$^+$]. Anal. calc for C$_{27}$H$_{31}$N$_4$Na$_4$O$_{18}$P$_3$: C, 36.67; H,3.53; N, 6.33. Found: C, 36.37; H, 3.81; N,6.10.

Modified dUTP 4i: N-Acetyl histidine was treated with N-hydroxysuccinimide (38 mg, 0.32 mmol) and 1,$^3$-dicyclohexycarbodiimide (49 mg, 0.24 mmol) in DMF (3 ml) at rt. After 12 hrs, the reaction mixture was filtered and the filtrate was added to a solution of sodium borate and DMF (1: 1) containing 4g (38 mg, 50 (mol). After 10 hrs at rt, the reaction mixture was evaporated to dryness and the residue was purified on reverse phase HPLC to give 32 mg (68%) of 4i. $^1$H-NMR (D$_2$O): (7.93 (s, bs,1H) H-6; 7.6–7.32 (m, 5H) phenyl and cinnamyl vinyl-H; 7.14 (d, br, 1H) imidazole-H; 6.75, 6.67 (d, br, 2H ) cinnamic vinyl-H and imidazole-H; 6.42–6.26 (d, 3H) allylamine vinylic protons and H-1'; 4.78 (s, br, H) H-3'; 4.23–4.03 (m, 8H) 5', 5" CH$_2$ and H-4', benzylic CH$_2$, and histidine -H; 3.00 (m, 2H) histidine -CH$_2$; 2.19 (m, 2H) H-2', 2"; 2.02 (s, 3H) N-acetyl CH$_3$. $^{13}$C-NMR (D$_2$O): (176.54; 175.22; 170.81; 166.80; 153.30; 143.24; 140.83; 140.29; 137.17; 137.08; 131.62; 131.45; 129.79; 129.51; 128.99; 124.58; 122.89; 114.68; 87.96; 87.80; 87.71; 72.71; 72.39; 67.73; 56.54; 45.05; 44.13; 41.15; 30.82; 24.13.$^{31}$P-NMR (D$_2$O): (-5.39 (d); -10.41 (d); -20.82 (t). MS (FT-MALDI): 884.1474, C$_{30}$H$_{38}$N$_7$O$_{17}$P$_3$Na$^+$(calcd 884.1435); 906.1301, C$_{30}$H$_{38}$N$_7$O$_{17}$P$_3$+2Na$^+$-H$^+$(calcd 906.1254).

EXAMPLE 4

Reverse Transcriptase Study

Reverse transcriptase assays: Template-directed extension was performed by addition of 10 pmol template DNA 5'-GCT AAA AAA GCT GCT AAA AAG CTG CTA AAA GCT GCT AAA GCT AAG CTA GCT CCC TTT AGT GAG GGT TAA TTG C-3' (SEQ ID NO. 1) to 10 pmol primer DNA 5'-GCA ATT AAC CCT CAC TAA AGG G-3' (SEQ ID NO 2) followed by Superscript II reverse transcriptase (Gibco, 200 units.(1$^{-1}$). The reaction (25 (I) contained 0.2 mM of dATP, dCTP, dGTP and 0.4 mM analog. Trace quantities of ((-$^{32}$P(-dATP was included to allow the extension efficiency to be monitored. All components except reverse transcriptase were combined, incubated at 90° C. and cooled to 37° C. to anneal the primer. The enzyme (600 units) was added and the reaction mixture was incubated at 37 (C. The DNA was precipitated in ethanol and then dissolved in gel-loading buffer containing urea and heated for 3 min at 90° C. After separation on a 10% denaturing acrylarnide gel, the samples were further analyzed with a Phosphorimager.

What is claimed is:

1. A compound of the structure below where wherein X is NH$_2$ or =O, where when X is NH$_2$, (H) is absent and - - - represents a chemical bond and when X is =O, - - - is absent and (H) is present representing a hydrogen bonded to N-1, C:C is a carbon-carbon double bond or a carbon-carbon triple bond, each R is independently hydrogen or a metal cation or wherein each R' is hydrogen or a metal cation and m is 1, 2 or 3, and R$_1$ is wherein R$_2$ is wherein $R_3$ is and n is an integer from 0 to 6.

2. The compound of claim 1 wherein n is 0, 1 or 2.

3. The compound of claim 1 wherein at least one R is a metal cation.

4. The compound of claim 3 wherein the cation is hydrogen or an alkali metal.

5. The compound of claim 4 wherein the alkali metal is sodium or potassium.

6. The compound of claim 1 where $-X$ is $=O$.

7. The compound of claim 1 wherein $R_1$ is

8. A DNA molecule comprising at least one nucleotide having the structure of the compound of claim 1.

9. A DNA molecule comprising at least one nucleotide having the structure of the compound of claim 6.

10. The DNA molecule of claim 8 that contains from about 5 to about 25 nucleotides.

11. The DNA molecule of claim 9 that contains from about 10 to about 20 nucleotides.

12. The DNA molecule of claim 9 that contains from about 5 to about 15 nucleotides.

* * * * *